United States Patent [19]

Sasaki et al.

[11] Patent Number: 4,841,992
[45] Date of Patent: Jun. 27, 1989

[54] TISSUE EXPANDER AND METHOD OF MAKING AND USING

[75] Inventors: Gordon H. Sasaki, Pasadena, Calif.; Eugene R. Jakubczak; John R. D. Gauger, both of Cordova, Tenn.

[73] Assignee: Dow Corning Wright Corporation, Arlington, Tenn.

[21] Appl. No.: 134,331

[22] Filed: Dec. 17, 1987

[51] Int. Cl.⁴ ............................................. A61B 19/00
[52] U.S. Cl. ........................................ 128/899; 623/8
[58] Field of Search ................ 623/7, 8, 11; 128/1 R, 128/899

[56] References Cited

U.S. PATENT DOCUMENTS

| | | | |
|---|---|---|---|
| 3,831,583 | 8/1974 | Edmunds, Jr. | 128/1 R |
| 4,157,085 | 6/1979 | Austad et al. | 128/1 R |
| 4,217,889 | 8/1980 | Radovan et al. | 128/1 R |
| 4,222,384 | 9/1980 | Birtwell | 128/349 B |
| 4,574,780 | 3/1986 | Manders | 128/1 R |
| 4,605,412 | 8/1986 | LaForest et al. | 623/8 |
| 4,643,733 | 2/1987 | Becker | 623/8 |
| 4,651,717 | 3/1987 | Jakubczak | 128/344 |
| 4,671,255 | 6/1987 | Dubrul et al. | 128/1 R |
| 4,685,447 | 8/1987 | Iversen et al. | 128/1 R |

FOREIGN PATENT DOCUMENTS 196821 10/1986 European Pat. Off. .

OTHER PUBLICATIONS

"Silastic(R) Differential Tissue Expander, H. P., Scalp Design", Product Sheet 117687T, Dow Corning Wright, Memphis, TN, 1987, 1 page, 2 sides.
"Reconstructive Mammary Implant (Birnbaum Design)", Data Sheet 120318, McGhan Medical Corporation, Santa Barbara, CA., Oct., 1977, 4 pages.
"Customized Reconstruction of the Breast after Radical and Modified Radical Mastectomies", article by Birnbaum, et al., in *The Western Journal of Medicine*, Nov., 1976, pp. 388–390.
*Principles of Polymer Systems*, by Ferdinand Rodriquez (New York: McGraw-Hill Book Company, 1970), pp. 45–46 and 217.
*Vulcanization of Elastomers* edited by G. Alliger, et al. (New York: Reinhold Publishing Corporation, 1964), pp. 77–89.
"Mentor Directa-Span ® Tissue Expander", Product Sheet 886-202, Mentor Corporation, Goleta, CA, Aug. 1986, 2 pages.

Primary Examiner—Richard J. Apley
Assistant Examiner—James Prizant
Attorney, Agent, or Firm—Susan M. Cornwall

[57] ABSTRACT

A tissue expander and a method of making a tissue expander which includes (a) a fluid-tight envelope which is inflatable by a single means for inflation and which has an expandable upper section formed (i) a first elastic portion and (ii) a second elastic portion formed of a material having a lower modulus of elasticity than that of the material forming the first portion, so that during the inflation of said envelope the modulus of elasticity of each portion at least partially controls the amount of expansion of each portion, thereby allowing the envelope to assume a complex shape. The tissue expander also has a means for inflating the envelope with a biocompatible fluid.

12 Claims, 3 Drawing Sheets

TISSUE EXPANDER AND METHOD OF MAKING AND USING

BACKGROUND OF THE INVENTION

The present invention relates to tissue expanders, including tissue-expanding mammary prostheses, and to methods of making and using such tissue expanders. More particularly, the invention relates to tissue expanders capable of expanding overlying tissue into a complex shape.

Subcutaneous tissue expanders have come into wide use because of the variety of plastic surgical procedures that have been developed which either require that tissue be expanded to receive or retain an implant or that a flap of tissue be generated for use on some other part of the body.

Of the tissue expanders known in the art, some provide for expanding tissue differentially, that is, into a preselected complex shape. For example, U.S. Pat. No. 4,574,780 to Manders discloses tissue expanders which are capable of differentially expanding skin. Manders discloses that the differential expansion can be accomplished by using a tissue expander having a limited expansion portion and a differential expansion portion. The patent teaches that one way of creating a limited expansion portion is by making the expander wall of that portion thicker than the differential expansion portion. Manders also discloses that the limited expansion portion may be created by reinforcing the portion. A commercial example of a tissue expander which uses the Manders invention is SILASTIC ® Differential Tissue Expander, H.P. sold by Dow Corning Wright, Arlington, Tennessee.

U.S. Pat. No. 4,651,717 to Jakubczak discloses another type tissue expander which is capable of expanding tissue into complex forms. This tissue expander consists essentially of at least two separately inflatable envelopes wherein one is used as a base and the other is smaller in volume than the first and is attached to the upper half of the base envelope to expand the tissue overlying the second envelope to a greater extend than is accomplished by the first envelope. This device requires that each envelope has an inflation means associated therewith that is separate from the other envelope's inflation means.

European Patent 196,821 discloses a tissue expander system wherein Dacron mesh may be embedded in members of the tissue expander to provide directional expansion of the tissue expander.

An implantable mammary prosthesis which can be partially inflated after the prosthesis is inserted beneath the skin is shown in product data sheet number 120318 dated 10/77 from the McGhan Medical Corporation of Santa Barbara, California, entitled "Reconstructive Mammary Implant (Birnbaum Design)" which shows a dual envelope mammary prosthesis where one part of the prosthesis has a gel-filled envelope and the other integral envelope along side the first is inflated with saline after implantation. Use of this prosthesis is described in a November, 1976, article entitled "Customized Reconstruction of the Breast After Radical and Modified Radical Mastectomies" by Birnbaum, et al. in The Western Journal of Medicine on pages 388–390. U.S. Pat. No. 4,643,733 to Becker discloses another implant which is a subcutaneous expander and a permanent reconstruction implant.

In the catheter art, U.S. Pat. No. 4,222,384 to Birtwell discloses a catheter formed from silicone rubber wherein the tip and balloon portion are molded in a single integral piece in a suitable mold but in a manner in which the tip portion of the mold is loaded with a parison of silicone rubber which will be stiff when cured and with the balloon portion of the mold being loaded with a parison of compatible silicone rubber which will be more elastic when cured.

In addition, U.S. Pat. No. 3,831,583 to Edmunds, Jr., et al. discloses an implantable device for restricting the flow of blood through a major blood vessel which includes (1) a ring, capable of inward distention, (2) a non-distensible bulb, and (3) a non-distensible tube. The patent also mentions that silicone rubber of varying degrees of hardness or cure can accommodate the need for the distensible or non-distensible portions.

SUMMARY OF THE INVENTION

In view of the tissue expander devices discussed above, there remains a need for a tissue expander which can shape overlying tissue into a complex shape and (1) can be made with existing manufacturing equipment, (2) whose characteristics can be easily altered to suit many applications, (3) is formed of biocompatible materials, (4) is relatively easy and quick to make and uses a minimum of parts, (5) can have a minimum number of injection sites therefore having a minimum number of injection button connections and minimizing the number of times a patient needs to be injected, (6) can have a uniform wall thickness, (7) is relatively economical, (8) has relatively low rejection rates during production, and (9) provides the surgeon with good control of differential expansion.

These and other objects can be provided by the implantable tissue expander of the invention which comprises (a) a fluid-tight envelope which is inflatable by a single means for inflation and which has an expandable upper section comprising a first elastic portion and a second elastic portion formed of a material having a lower modulus of elasticity than the material forming the first portion, so that during the inflation of the envelope the modulus of elasticity of each portion at least partially controls the amount of expansion of each portion and causes the envelope to assume a complex shape, and (b) means for inflating the envelope with a biocompatible fluid associated therewith for the controlled inflation of the envelope. The tissue expanders of the invention are also suitable for inflatable-type mammary prostheses. The invention also provides a method of making an envelope for such a tissue expander and a method of using such a tissue expander.

BRIEF DESCRIPTION OF THE DRAWINGS

The above and other objects and advantages of the present invention will become apparent to those skilled in the art upon an examination of the following description and drawings which are illustrative of the present invention.

In the Drawings.

DETAILED DESCRIPTION OF THE INVENTION

Figure 1:
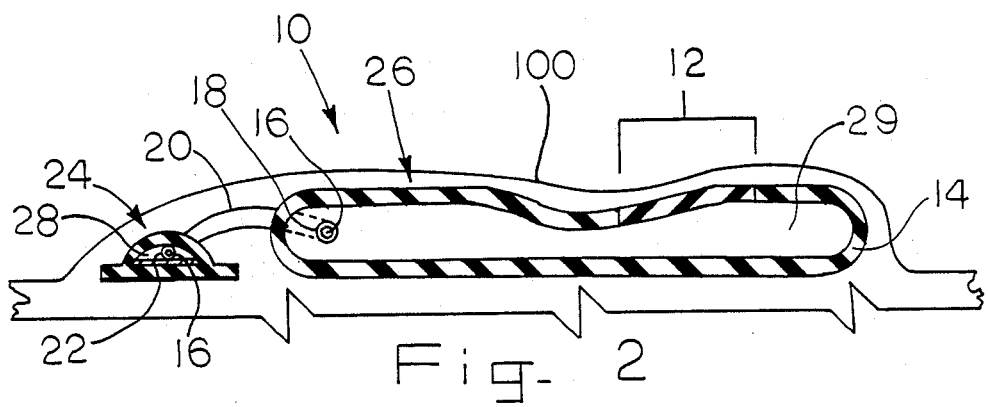
FIG. 1 is a partial cross-sectional side view of one embodiment of the present invention shown as a substantially deflated tissue expander.

Referring to the Drawings, wherein like reference characters designate corresponding parts throughout the Figures thereof, FIG. 1 depicts one form of a tissue expander according to the invention shown as tissue expander 10 implanted beneath the skin 100 of a patient. Tissue expander 10 consists of a fluid-tight envelope 26 and means for inflating the envelope 26. The inflation means is shown in the form of injection button 24 of conventional design which is designed to permit inflation by addition of a biocompatible fluid such as isotonic saline into pocket 29 of envelope 26. As with such conventional injection buttons, a hypodermic syringe needle is used to introduce biocompatible fluid into the hollow region 28 of injection button 24. The fluid travels through the lumen of tube 20 from region 28 into pocket 29 of envelope 26 because the ends of tube 20 are sealed to injection button 24 and envelope 26 at attachment points 22 and 18, respectively, with, for example, a medical grade silicone adhesive such that the lumen 16 is in communication with region 28 and pocket 29.

Envelope 26 is formed from a bottom and an expandable upper section which together define pocket 29 which is inflatable by a single means for inflation. Means for inflation is shown as injection button 24. The expandable upper section has portions 12 and 14, both made of elastic material with portion 12 being formed of a material having a lower modulus of elasticity than the material from which portion 14 is formed. Although it is illustrated that the bottom of envelope 26 is formed of the same material as portion 14, this is not required for the invention. The bottom may be made of the same or different material than any other part of the expander.

Figure 2:
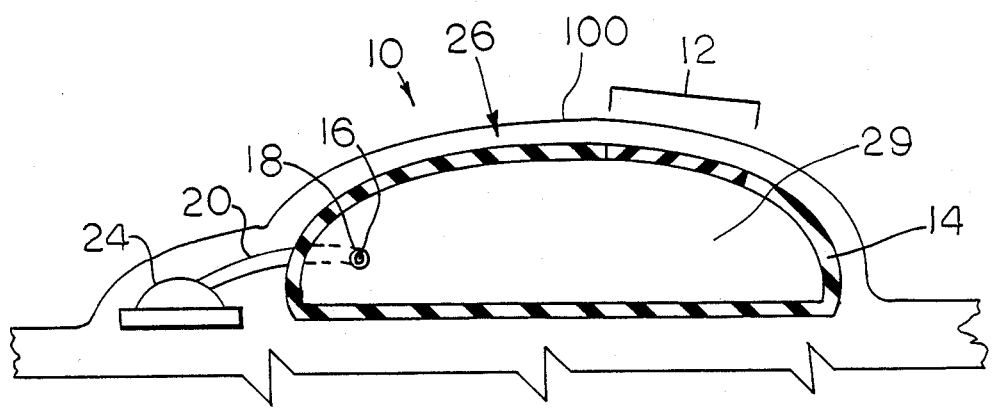
FIG. 2 is a partial cross-sectional side view showing the tissue expander of FIG. 1 after partial inflation.

FIG. 2 illustrates tissue expander 10 after some inflation. FIGS. 2-3 and 5-8 show the pockets inflated, but no inflation fluid is shown, for purposes of clarity. The fluid used in inflate the envelopes is preferably an isotonic saline solution although other bicompatible fluids which will remain under pressure within the envelope, such as a silicone gel, can also be used. In FIG. 2, portion 12 has not begun to expand at a faster rate than portion 14, and therefore envelope 26 has a generally smooth hemispherical shape. Resulting from the expansion of the envelope 25, skin 100 also has expanded and taken on the same general shape of envelope 26. The appearance of the tissue expanders of this invention will vary depending on the design and the materials used, therefore, the generally smooth shape is not necessarily achieved with every tissue expander of the invention, but is shown here as a possible occurrence and for illustrational purposes.

Figure 3:
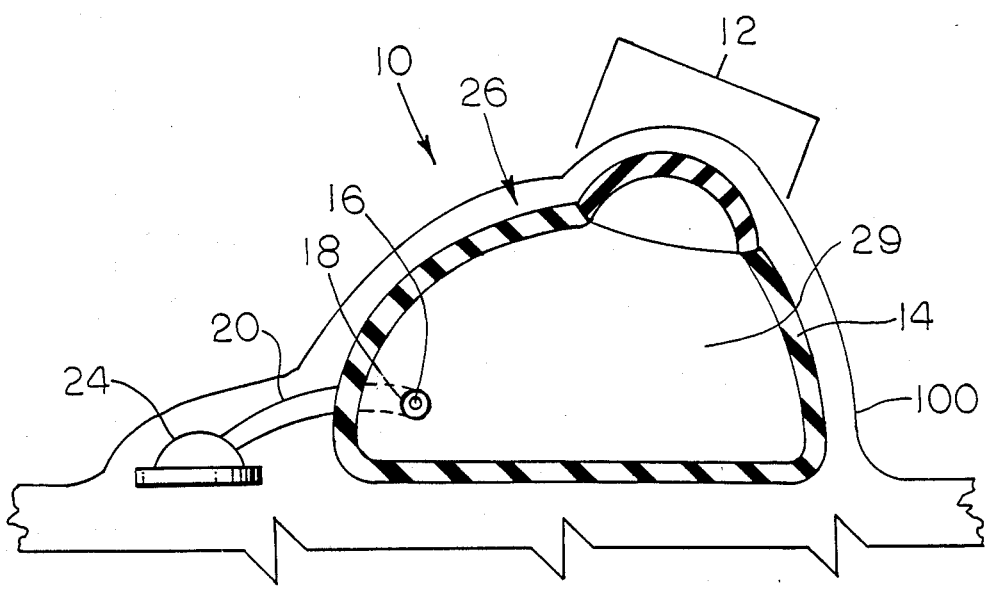
FIG. 3 is a partial cross-sectional side view showing the tissue expander of FIG. 2 after further inflation.

FIG. 3 illustrates expander 10 which has been inflated to a greater degree than that shown in FIG. 2, wherein portion 12 has expanded more than portion 14 and therefore has caused envelope 26 and skin 100 to each assume a complex shape. This illustrates that the modulus of elasticity of each portion controls the amount of expansion of each portion. Stated another way, the different moduli of elasticity of the portions causes one portion to expand to a greater extent than the other portion some time during the expansion process. It is not necessary that the portion having the lower modulus expand to a greater extent throughout the entire inflation process, but at least during some period of the process. As can be seen with FIGS. 1-8, the envelope does not need to have varying wall thickness to achieve differential expansion.

In this example, portion 12 stretches at a faster rate than portion 14. It is not necessary that portion 12 stretch at a faster rate than portion 14 throughout the entire inflation process, but when portion 12 stretches at a faster rate during at least part of the inflation process the envelope is expanded more at portion 12 than at portion 14 to achieve the differential expansion. Also, it is not necessary that one portion expands at a "faster rate" than another; two portions can expand at the same rate and achieve differential expansion. For example, an envelope formed of one material which when filled, but not yet expanded or stretched, has a first end which measures 1" high and a second end which measures 2" high. It is feasible that this envelope when stretched will take on a generally spherical shape so that each end has generally the same height. In contrast, when using the invention and making a similar envelope but where the first end is made from a material having a higher modulus of elasticity than the second end, expansion could result so that after some inflation the 1" high end expands to a height of 1 ½" and the 2" end expands to a height of 3". In this example, the moduli of elasticity of the materials controls the amount of expansion even though the two ends have expanded at the same rate over period of time: a 50% increase in height for each end.

Figure 4:
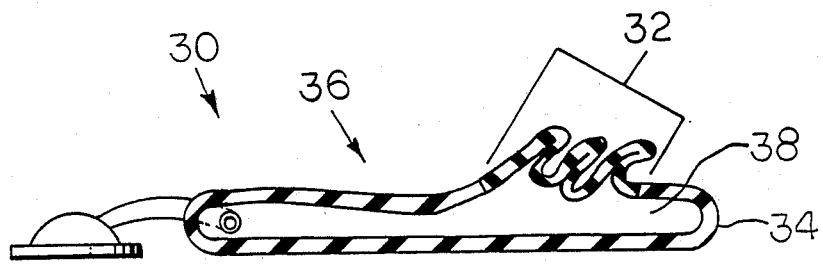
FIG. 4 is a partial cross-sectional side view illustrating a second embodiment of the present invention shown as a substantially deflated tissue expander.
Figure 5:
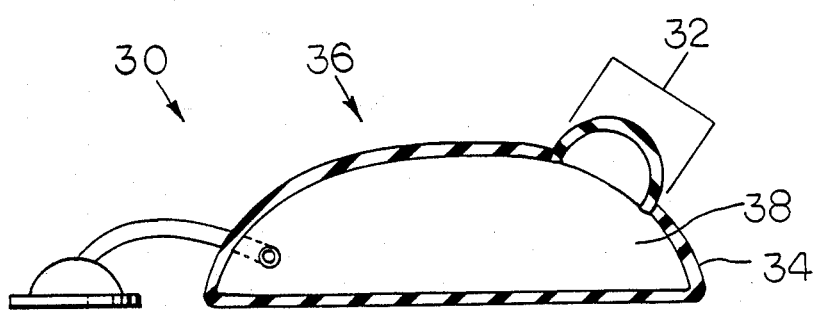
FIG. 5 is a partial cross-sectional side view showing the tissue expander of FIG. 4 after partial inflation.
Figure 6:
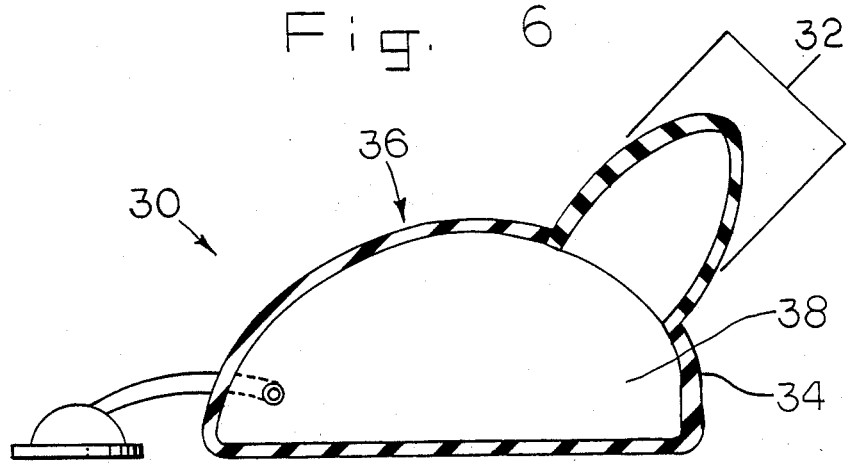
FIG. 6 is a partial cross-sectional side view showing the tissue expander of FIG. 5 after further inflation.

FIGS. 4-6 illustrate another type of tissue expander according to the invention. FIG. 4 shows tissue expander 30 having envelope 36. Envelope 36 is formed of a bottom and an upper section, and the upper section is formed of portions 32 and 34, wherein portion 32 is formed of a material having a lower modulus of elasticity than the material which forms portion 34. In this embodiment, envelope 36 is pre-formed so that portion 32 has excess material and has folds when the envelope is in its deflated state.

FIG. 5 shows expander 30 after inflation of envelope 36. As can be seen in this illustration, portion 32 has already caused envelope 36 to take on a complex shape because the excess material has been filled with fluid. In FIG. 6, envelope 36 has been inflated beyond that shown in FIG. 5, showing that portion 32 has expanded relatively more than portion 34 and has caused envelope 36 to take on a different shape than that shown in FIG. 5.

Figure 7:
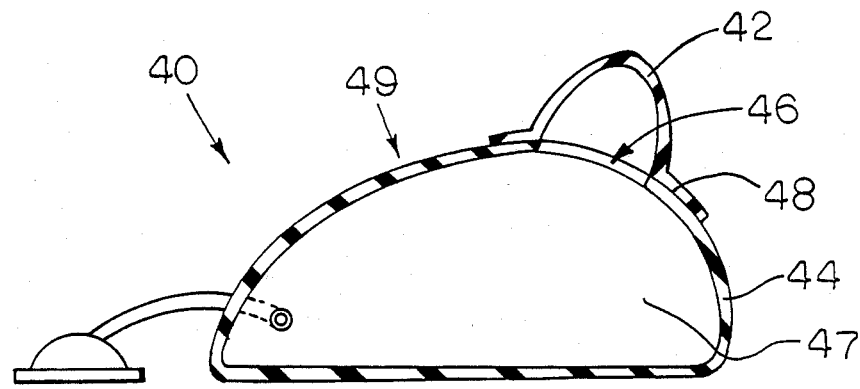
FIG. 7 is a partial cross-sectional side view illustrating a third embodiment of the present invention shown as an inflated tissue expander.

FIG. 7 illustrates another embodiment of the invention shown as tissue expander 40 having envelope 49. Envelope 49 is shown in the inflated state. In this embodiment, portion 42 has a lower modulus of elasticity than portion 44. Portion 42 is adhered onto portion 44 at an opening 46 in portion 42 which provides fluid communication between the spaces covered by portions 42 and 44. Portion 42 may be adhered by bonding to portion 44 or it may be adhered by using an adhesive between portions 42 and 44 at area of contact 48. As an example, a medical grade silicone adhesive can be used to adhere the two portions if silicone elastomers are used for the envelope. Alternatively, portion 42 could be laminated to the inside surface of portion 44, so long as it is placed below an opening in portion 44.

Figure 8:
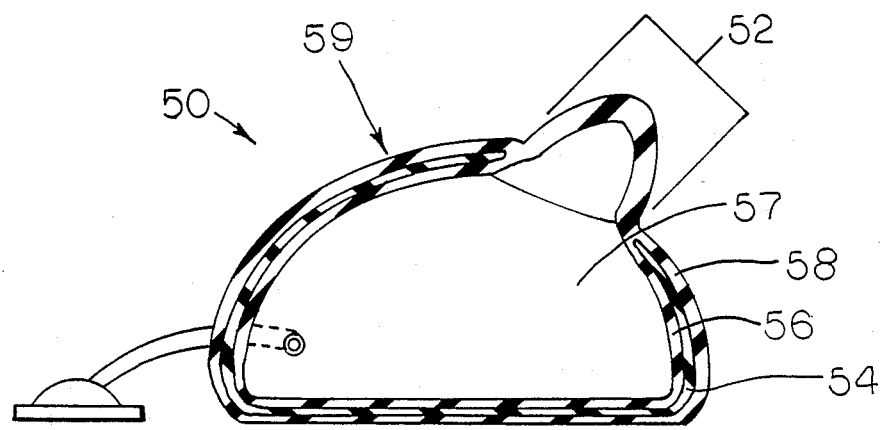
FIG. 8 is a partial cross-sectional side view illustrating a fourth embodiment of the present invention shown as an inflated tissue expander.

FIG. 8 illustrates a preferred embodiment of the invention shown as tissue expander 50 with envelope 59. Envelope 59, shown in the inflated state, has an inside elastic layer 56 which extends around the entire envelope, an intermediate elastic layer 54 which extends only partially around the envelope, and an outside layer 58 which extends around the entire envelope. Inside layer 56 and outside layer 58 are formed of the same material, whereas intermediate layer 54 is formed of a material having a higher modulus of elasticity than the other two layers. The area of envelope 59 which is deficient of the material which forms layer 54 expands further than the remainder of envelope 59, because the composite of the remainder of the envelope includes a material which has a high modulus of elasticity than the area of envelope 59 which is deficient of layer 54.

Envelope 59 is prepared by first coating a mandrel with a layer of a first polymeric composition, then coating almost all of the coated mandrel with a second polymeric composition which has a higher modulus of elasticity than the first composition leaving a space on the coated mandrel uncoated with the second composition, and then coating the mandrel with the first composition again so that the space left uncoated with the second composition is covered with the first composition. The composite compositions are then cured and removed from the mandrel. It is preferred that silicone elastomer compositions are used for the first and second compositions and, if they are used, generally the compositions will bond together upon curing. However, the two compositions do not necessarily have to be capable of bonding together.

Variations on this technique are possible. For example, one could eliminate the inside layer 56 or the outside layer 58 altogether and achieve similar results. One could also use three or more polymeric compositions each with different moduli of elasticity, so long as at least one area of the envelope has a lower modulus of elasticity than the envelope wall surrounding that area, so that a complex shape may be achieved.

Although the figures illustrate the combination of only two portions to form the expandable upper section, one being formed of a material having a lower modulus of elasticity than the other, devices of the invention may include more than two portions, where the materials forming the portions could each have a different modulus of elasticity.

The invention is also suitable for making inflatable mammary prostheses which are implanted, used to differentially expand tissue, then left in the body as prostheses. For example, such as mammary prosthesis could be similar to any of the expanders shown in the FIGS. 1-8. Another proposed design would be to have a double lumen mammary prosthesis having a chamber inside another chamber, where one chamber is optionally pre-filled with a gel. The unfilled chamber would be composed of at least two materials having different moduli of elasticity to provide for the differential expansion. Preferably, the unfilled chamber is the interior chamber and the gel-filled chamber is the exterior chamber. Having the gel-filled chamber on the outside would help protect the interior chamber and, in case of a rupture, help minimize leaking of the fluid used to fill the interior chamber. A tissue expander or a mammary prostheses using this invention may also have side-by-side or stacked chambers where one is pre-filled or neither is pre-filled.

The tissue expander of the invention may have a remote injection button as shown in the figures or may have an injection button mounted directly on the envelope. One example of an injection button which can be used with this invention is found in U.S. Pat. No. 4,190,040 to Schulte. Another injection button which can be used on the envelope is of the type described in U.S. Pat. No. 4,428,364 to Bartolo. As an alternative to using percutaneous means for inflating the tissue expander, one could use the teachings of Austad in U.S. Pat. No. 4,157,085 which teaches osmotically expandable tissue expanders. The bottom of the envelopes may be substantially non-extensible, e.g., using the teaching of Radovan in U.S. Pat. No. 4,217,889.

Although it is illustrated in the figures that the portion formed of the material with the lower modulus of elasticity is smaller than the other portion, envelopes according to this invention may be formed where the larger portion is formed of the material with the lower modulus of elasticity.

The envelopes of this invention can also be formed with varying wall thicknesses or embedded materials for limiting expansion so that the expansion of the envelope is controlled by both the moduli of elasticity of the materials of construction and another means. There are several advantages of making the envelopes according to this invention whether or not in combination with other ways of controlling expansion. Envelopes of this invention have the potential of being relatively thinner than envelopes solely using varying wall thicknesses to control expansion and still achieve the desired amount of differential expansion. Therefore envelopes of this invention can use less material and reduce the cost of making, can be faster and easier to make because thinner walls require less application of the polymeric composition of a mandrel, if a mandrel is used, and can cure faster than the thicker envelopes. In addition, when less material and/or fewer applications of the material are required to make the envelopes there is less change for dirt pick-up and bubble formation between applied layers and therefore improved overall quality of the envelope results.

The envelopes of this invention are preferably constructed of biocompatible silicone elastomers similar to the medical grade silicone elastomers commonly used in the manufacture of mammary implants or tissue expanders (e.g. those which are available from Dow Corning Corporation, Midland, MI 48686), but could be manufactured of other biocompatible elastic materials, such as polyurethanes. It is preferred that silicone elastomers which cure via $\equiv$SiH to $CH_2=CHSi\equiv$ addition, in the presence of a catalyst, such as a platinum catalyst, are used. When using silicone elastomers as the materials for forming portions 12 and 14, the level of the filler, preferably, fumed silica, to control the modulus of elasticity has been found to work well. The envelopes can be formed in various ways, e.g. by applying a suitable solution to a mandrel as discussed or, in the case of silicone envelopes, by adhering two sheets of vulcanized elastomer together by imposing an unvulcanized washer between the sheets at the perimeter and curing the washer to the elastomer sheets while applying pressure to the perimeter.

As discussed previously, portion 12 is formed of a material having a lower modulus of elasticity than the material used to form portion 14. Modulus of elasticity can be defined as the applied force per unit of original cross sectional area of a test bar of the material at a specific percentage elongation (or tensile stress at a given elongation). Although any difference in tensile stress at a given elongation would suffice for the invention, we have found that a silicone elastomer for portion 12 having a tensile stress of about 200 psi at 100% elongation works well with a silicone elastomer for portion 14 having a tensile stress of about 500–700 psi at 100% elongation. The tensile stresses were measured by a procedure based on ASTM D 412. In this case, the modulus of elasticity of the more elastic material is, as preferred, less than half of the modulus of elasticity of the less elastic material. Using materials wherein one has a modulus of elasticity of less than about 75% than the other would also be highly suitable.

As mentioned, a preferred way of making materials having a difference in moduli of elasticity is by changing the level of filler in the polymeric compositions. By adding more filler to a composition, the modulus of elasticity is increased, resulting in a stiffer material. For example, on page 217 of the book, *Principles of Polymer Systems* (1970), by Ferdinand Rodriguez, the effect of fillers on polymer characteristics is discussed along with the fact that the addition of carbon black in a cross-linked natural rubber shows an increase in stiffness with increase in filler loading.

Another way of forming materials with varying moduli of elasticity is by varying the crosslinks density (or level of cure) or molecular weight with or without changes in filler level, wherein generally, compositions, with higher crosslink density have higher moduli. The phenomenon of altering the modulus of elasticity with changes in crosslink density or level of cure is discussed on pages 77–89 of the book, *Vulcanization of Elastomers* (1964), edited by G. Alliger and I. J. Sjothun. Another way of acquiring two materials with different moduli is by using materials which have a different polymer base, e.g. where one portion is formed from silicone-polyurethane copolymers and the other is silicone. Another way is by the addition of plasticizers one can create a material with a lower modulus of elasticity. This phenomena is discussed on pages 45–46 of *Principles of Polymer Systems*.

To make the envelopes of the invention any known fabrication technique may be used. For example, the envelopes can be formed by coating a mandrel (by spraying, brushing, dipping, rolling, etc.) with an uncured polymeric composition and, subsequently, curing the composition, or they may be formed by adhering two sheets of elastic material together. When the envelope is formed by using a mandrel with rounded edges, the envelope has the further advantage of not having any sharp, rigid, or elevated edges which may cut into the patients's tissue and cause discomfort and/or other complications. The portions of the upper section responsible for the differential expansion, may be adhered to the envelope by bonding or adhering two bodies of material together with a suitable adhesive.

Having described several embodiments of the tissue expander, the manner in which it can be used will now be described with reference to FIGS. 1–3. It is to be understood that tissue 100 would rest directly upon expander 10 and button 24 when expander 10 is implanted. In FIG. 1, a partial cross-sectional side view of substantially deflated tissue expander 10 is shown implanted beneath tissue 100 to be expanded according to surgical procedures familiar to those skilled in the art of implantation of tissue expanders. Tissue expander 10 is placed in a surgically-formed opening beneath tissue 100. If means for attaching tissue expander 10 are present it would be used to attach the device to underlying body members and thus help hold envelope 26 in a preselected orientation with respect to the tissue to be expanded. Such means could be, for example, fixation tabs which can be strips of polyester fiber mesh reinforced silicone elastomer fixed to the lower portion of the envelope such as by means of a medical grade silicone adhesive. These tabs would then be sutured to underlying body members, e.g. muscle or fascia. A needle of a hypodermic syringe which contains a biocompatible fluid is then passed through tissue 100 and injection button 24 and then fluid is gradually forced into hollow region 28 and, in turn, travels through tube 20 and into interior region 29 of envelope 26. Such injections are done periodically over an extended period of time. Envelope 26 is inflated with the biocompatible fluid in a well known manner at such a rate that the tissue 100 is expanded over a reasonably short period of time, but not so short a time that tissue necrosis occurs. FIG. 2 shows tissue expander 10 after some inflation and FIG. 3 shows tissue expander 10 after inflation beyond that shown in FIG. 2 and enough inflation to see differential expansion, resulting in the tissue taking on a complex shape.

After the envelope has been inflated to the desired degree, tissue expander 10 may be surgically removed and a prosthesis may be surgically implanted in its place or the expander may be left in as a prosthesis.

These and other variations of the present invention may be made which fall within the scope of the appended claims even though such variations were not specifically discussed above.

That which is claimed is:

1. A tissue expander comprising
  (a) a fluid-tight envelope which is inflatable by a single means for inflation, said envelope having an expandable upper section comprising
    (i) a first elastic portion formed of a first elastomer and
    (ii) a second elastic portion formed of a second elastomer having a lower modulus of elasticity than that of said first elastomer and wherein the elastomers which form said portions have different levels of finely divided solid filler, so that during the inflation of said envelope the modulus of elasticity of each elastomer at least partially controls the amount of expansion of each portion and causes the envelope to assume a complex shape, and
  (b) means for inflating said envelope with a biocompatible fluid associated therewith for the controlled inflation of said envelope.

2. A tissue expander as claimed in claim 1 wherein the modulus of elasticity of said second elastomer is less than 75% of that of said first elastomer.

3. A tissue expander as claimed in claim 1 wherein the modulus of elasticity of said second elastomer is less than half of that of said first elastomer.

4. A tissue expander comprising
  (a) a fluid-tight envelope which is inflatable by a single means for inflation, said envelope having an expandable upper section comprising (i) a first elastic portion formed of a first elastomer and (ii) a second elastic portion formed of a second elastomer having a lower modulus of elasticity than that of said first elastomer and wherein the elastomers which form said portions have different levels of crosslink density, so that during the inflation of said envelope the modulus of elasticity of each elastomer at least partially controls the amount of expansion of each portion and causes the envelope to assume a complex shape, and (b) means for inflating said envelope with a biocompatible fluid associated therewith for the controlled inflation of said envelope.

5. A tissue expander as claimed in claim 4 wherein the modulus of elasticity of said second elastomer is less than 75% of that of said first elastomer.

6. A tissue expander as claimed in claim 4 wherein the modulus of elasticity of said second elastomer is less than half of that of said first elastomer.

7. A tissue expander comprising (a) a fluid-tight envelope which is inflatable by a single means for inflation, said envelope having an expandable upper section comprising (i) a first elastic portion formed of a first elastomer and (ii) a second elastic portion formed of a second elastomer having a lower modulus of elasticity than that of said first elastomer and wherein said second elastomer contains a plasticizer not present in said first elastomer, so that during the inflation of said envelope the modulus of elasticity of each elastomer at least partially controls the amount of expansion of each portion and causes the envelope to assume a complex shape, and (b) means for inflating said envelope with a biocompatible fluid associated therewith for the controlled inflation of said envelope.

8. A tissue expander as claimed in claim 7 wherein the modulus of elasticity of said second elastomer is less than 75% of that of said first elastomer.

9. A tissue expander as claimed in claim 7 wherein the modulus of elasticity of said second elastomer is less than half of that of said first elastomer.

10. A tissue expander comprising (a) a fluid-tight envelope which is inflatable by a single means for inflation, said envelope having an expandable upper section comprising (i) a first elastic portion formed of a first elastomer and (ii) a second elastic portion formed of a second elastomer having a lower modulus of elasticity than that of said first elastomer and wherein the elastomers which form said portions are made from different polymer bases, so that during the inflation of said envelope the modulus of elasticity of each elastomer at least partially controls the amount of expansion of each portion and causes the envelope to assume a complex shape, and (b) means for inflating said envelope with a biocompatible fluid associated therewith for the controlled inflation of said envelope.

11. A tissue expander as claimed in claim 10 wherein the modulus of elasticity of said second elastomer is less than 75% of that of said first elastomer.

12. A tissue expander as claimed in claim 10 wherein the modulus of elasticity of said second elastomer is less than half of that of said first elastomer.

* * * * *